United States Patent
Wells et al.

(10) Patent No.: US 6,681,703 B2
(45) Date of Patent: Jan. 27, 2004

(54) TILTABLE TABLE

(75) Inventors: Peter J Wells, Minchinhampton (GB); David R McMurtry, Dursley (GB)

(73) Assignee: Renishaw PLC, Gloucestershire (GB)

( * ) Notice: Subject to any disclaimer, the term of this patent is extended or adjusted under 35 U.S.C. 154(b) by 0 days.

(21) Appl. No.: 10/101,375

(22) Filed: Mar. 20, 2002

(65) Prior Publication Data

US 2002/0148392 A1 Oct. 17, 2002

(30) Foreign Application Priority Data

Mar. 21, 2001 (GB) ............................................. 0106977

(51) Int. Cl.[7] ............................................... A47B 85/00
(52) U.S. Cl. ................... 108/20; 108/1; 108/4
(58) Field of Search ............... 108/20, 21, 22, 108/1, 2, 4, 6, 7, 8, 9; 74/16

(56) References Cited

U.S. PATENT DOCUMENTS

| | | | |
|---|---|---|---|
| 369,233 A | * 8/1887 | Coxe et al. ................. 74/86 |
| 3,744,902 A | * 7/1973 | Henker ...................... 355/53 |
| 3,836,162 A | * 9/1974 | Felkner .................... 248/188.3 |
| 3,958,659 A | * 5/1976 | Selman ..................... 180/89.15 |
| 4,180,002 A | * 12/1979 | Huempfner .................... 108/6 |
| 4,244,547 A | * 1/1981 | Kooi ....................... 248/180.1 |
| 5,340,111 A | * 8/1994 | Froelich ..................... 473/279 |
| 5,398,620 A | * 3/1995 | Rouch ......................... 108/1 |
| 5,505,422 A | * 4/1996 | Elterman .................... 248/476 |
| 5,780,943 A | * 7/1998 | Ono .......................... 310/12 |
| 5,890,436 A | * 4/1999 | Thompson ..................... 108/7 |
| 6,408,767 B1 | * 6/2002 | Binnard et al. ............... 108/20 |

FOREIGN PATENT DOCUMENTS

CH         653464 A5 * 12/1985

OTHER PUBLICATIONS

Braddick, "Mechanical Design of Laboratory Apparatus", Chapman & Hall, London, 1960, pp. 11–30.

* cited by examiner

*Primary Examiner*—Jose V. Chen
(74) *Attorney, Agent, or Firm*—Oliff & Berridge, PLC

(57) ABSTRACT

A tiltable table 10 is shown having (in this embodiment) two tilt positions to which top 20 and base 30 are repeatably repositionable. Support parts 32, 34, 36 and 38 provide a kinematic support in both of the two positions. Further embodiments provide more than two tilt positions. Positions are held by magnetic attraction, here, magnets, 40 and 42.

11 Claims, 3 Drawing Sheets

Section VV

TILTABLE TABLE

BACKGROUND OF THE INVENTION

1. Field of the Invention

The invention relates to a table for supporting an object, the table being tiltable to two, or more predetermined positions.

During the analysis or manufacture of parts, particularly those with complex 3D shapes, it is often desirable to reorientate either the part or the device doing the analysis/manufacturing so that that part can be analysed or produced more conveniently.

2. Description of the Prior Art

One way of reorientating the part or the device is to have it mounted to a tiltable table. However, in many applications accurate and repeatable positioning of the table is required, for example when the table is put back to the same position several times. Common machining tilt tables do not allow repeatable accurate repositioning. Often such tables have a simple pivotable plate on which to mount work and an angular scale to show the amount of tilting.

SUMMARY OF THE INVENTION

A tiltable table according to the invention comprises two elements which are movable relative to each other into two or more predetermined positions, each element having mutually co-operable parts, the table being characterised in that either the parts provide a kinematic support between the two elements when the elements are in any one of the positions, or in that the parts provide no more than six points of contact between the two elements when the elements are in any one of the positions and in that the parts restrict the relative movement of the elements.

Embodiments of the invention thus allow for tilting of the two elements relative to each other into a plurality of positions and either the kinematic support or the three points of contact allow repeatable repositioning into the positions.

Preferably there are two or four positions and the elements are held in any one of the two or more positions by magnetic attraction.

Preferably the tiltable table forms part of a machine and the machine has an actuator for tilting, the table. The actuator may be a solenoid, a pneumatic or hydraulic movement device or may be a movable part of the machine used as a pusher e.g. a measurement probe or cutting tool.

BRIEF DESCRIPTION OF THE DRAWINGS

The invention will now be described with reference to the drawings, in which.

DESCRIPTION OF THE PREFERRED EMBODIMENTS

Figure 1:
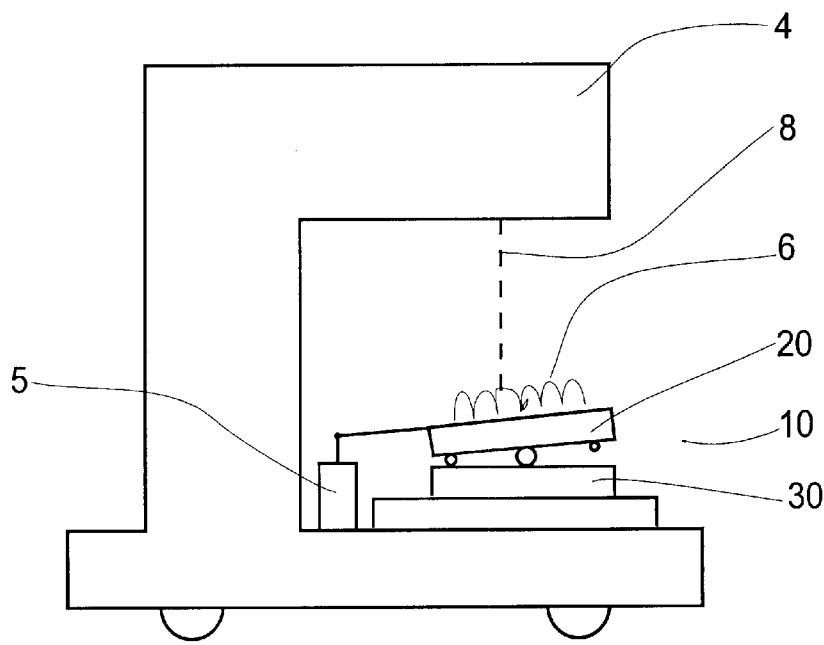
FIG. 1 shows a tiltable table mounted, on a scanning machine.

FIG. 1 shows a typical example of an application of the tiltable tables of the invention shown in FIGS. 2–5. Table 10 is being used to tilt a workpiece 6, for example a dental impression, so that scanning machine on which the table is mounted can follow and record the profile of the whole of the workpiece, particularly areas which could not be scanned if the workpiece were not tilted.

FIG. 1 shows a laser scanning machine, but any non-contact or contact scanning or coordinate measurement can be assisted by a tiltable table according to the invention.

Usually a tilt of about 10–15° between a base element 30 and a top element 20 will be adequate for dental impressions but using the tiltable table of the invention it is possible to obtain a tilt of 60° or more.

Figure 2:
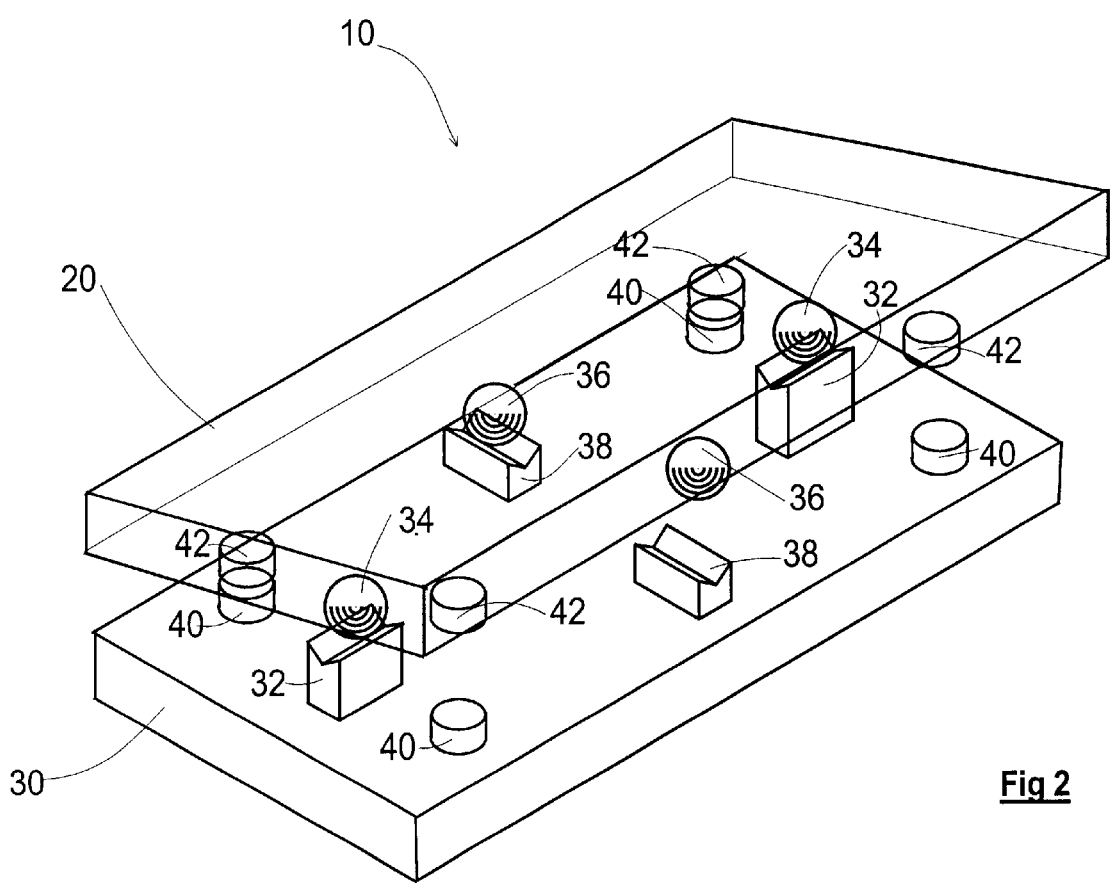
FIG. 2 shows a two-position tiltable table according to the invention.

FIG. 2 shows one embodiment of the invention. There is shown a tiltable table 10 having top and base elements 20 and 30 (in all the Figures the top is shown in outline only, so that the parts under it can be seen more clearly). These elements can, in use, be angularly repositioned with respect to each other so that repositioning of anything which is carried for example on the top element is possible.

In this embodiment two vee-blocks having grooves 32 are supported on the base 30 and two balls 34 supported on the top 20 sit in the grooves. The balls 34 locate on each side of the respective vee groove 32. These balls and grooves allow a rocking motion between two positions defined by stops. The stops are formed from two balls 36 and two vee-blocks 38. One block and ball co-operate on each side of the rocking axis formed between the centers of the two balls 34, to locate the top in one of two positions. FIG. 2 shows the top in one of those positions. In this example balls 34 and 36 are supported on the top and vee-blocks 38 are supported on the base.

The top is held in one of these positions mentioned immediately above by the attraction between a set of magnets 40 and 42.

It can be seen from FIG. 2 that in any on of the two tilted positions of the top that six points of contact are made between the top and the bottom (two for each of the three balls 34, 34 and 36). Thus a kinematic location of the top and base is achieved.

If the base 30 is fixed securely then the top can be positioned repeatedly in either of the two positions.

If two (or more) of these tables are placed one on top of the other with their respective rocking axes offset, then the top element of the uppermost table will have four (or more) tiltable positions.

Figure 3:
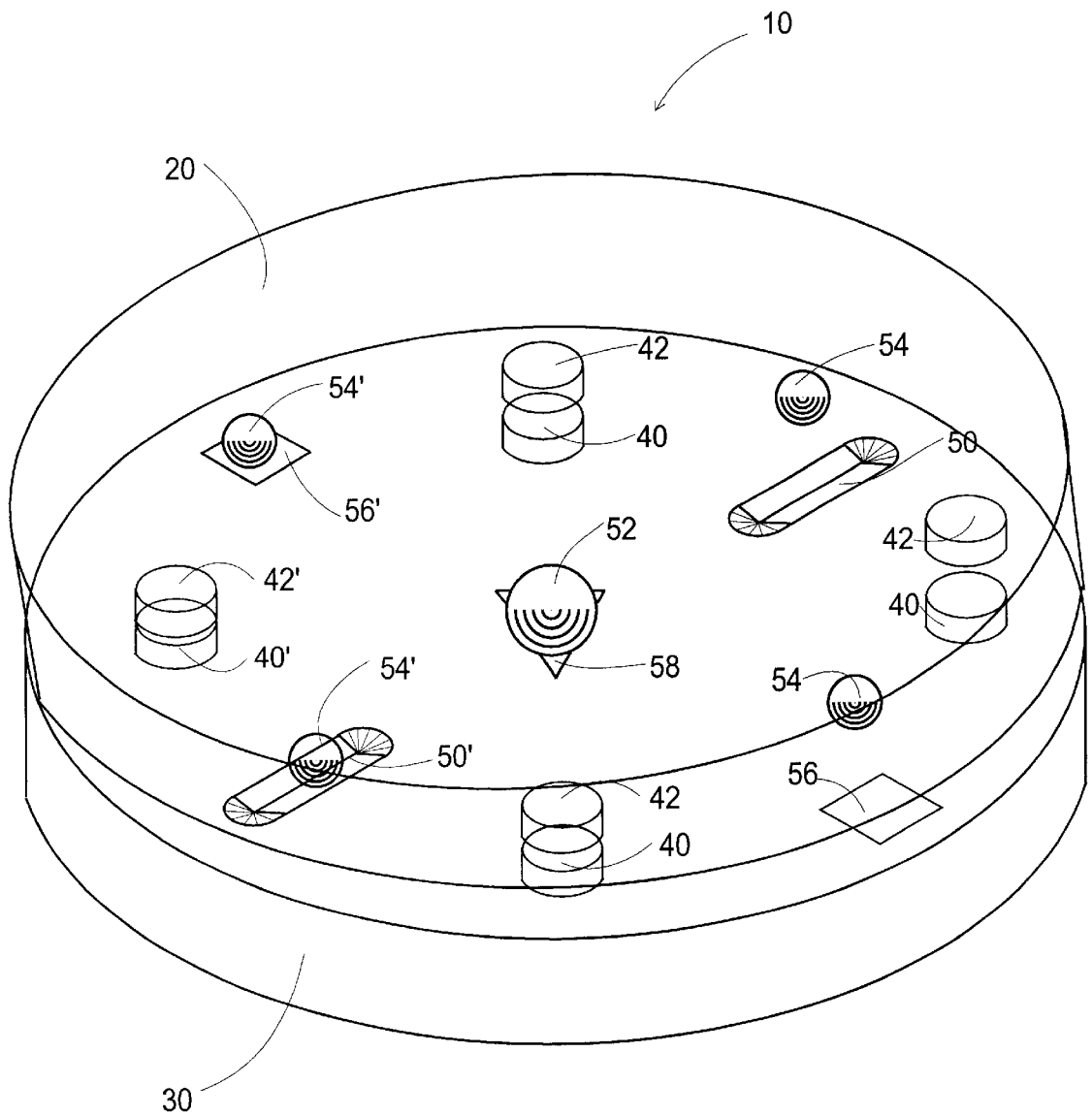
FIGS. 3 and 4 show four-position tiltable tables according to yet another two embodiments of the invention.

FIG. 3 shows another embodiment of the invention. In this instance the top and base are relatively position able into four positions. Each of the four positions are defined by six points of contact between the top 20 and the base 30. Two of the points of contact are made by the seating of a ball 54' supported on the top 20 within a vee-groove 50' in the base. Another one contact point is formed between ball 54' and a flat pad 56' and another three contact points are formed between a central ball 52 and the three sloping aides of a triangular recess 58. Thus six points of contact in all are obtained in any one of four possible tilt positions of the top 20 relative to the base 30.

Magnet pair 40' and 42' holds the position illustrated. In the Figure, the top is shown tilted to the left so the balls 54' are seated in a vee-groove 50' and on a pad 56' whereas balls 54 are not seated. It will be apparent from the drawing that the further three tilt positions can be obtained when another pair of balls 54 are seated at their respective grooves 50 and pads 56. A magnet pair 42, 40 will hold that position.

Figure 4:
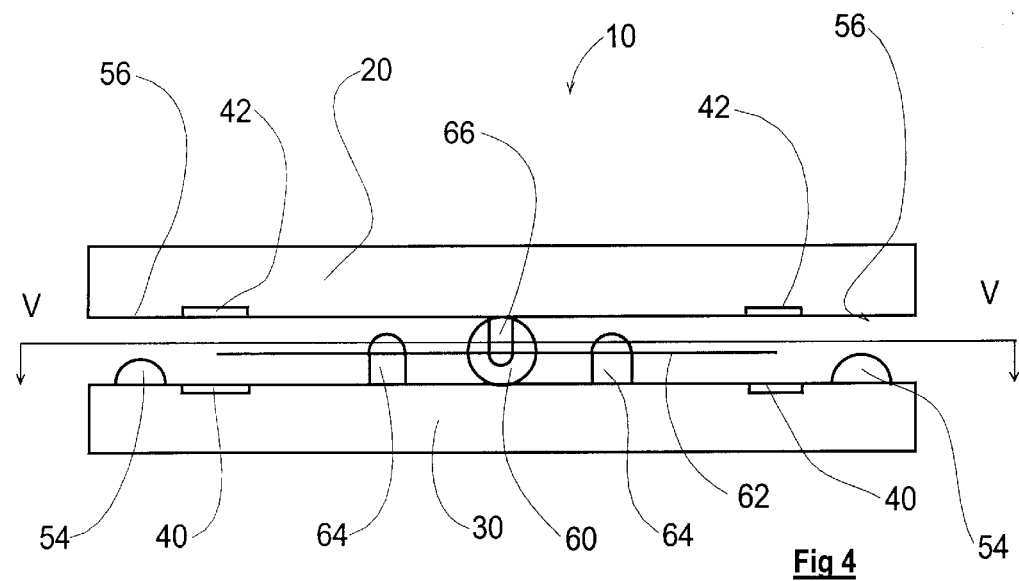
Figure 5:
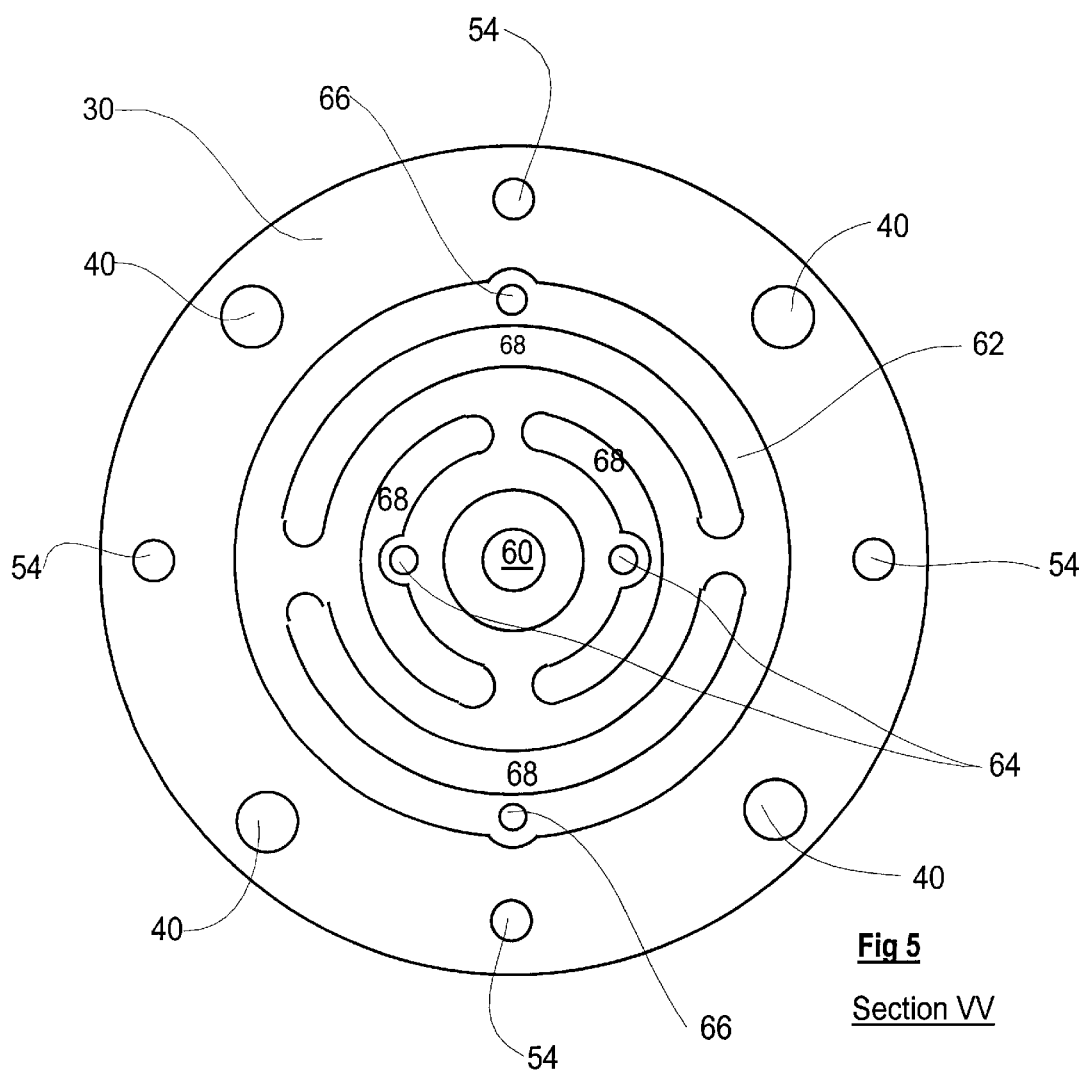
FIG. 5 shows a section along line V—V of the four-position tiltable table of FIG. 4.

FIGS. 4 and 5 show another embodiment of the invention. FIG. 4 shows a tilt table 10 in a mid position i.e. not located in one of its tilt positions, and FIG. 5 is a section along the line V—V in FIG. 4.

In this embodiment top 20 is able to rock on a ball 60 fixed to the base 30. The rocking motion is delimited by the contact of two adjacent balls 54 on base 30 with respective opposed flat contact surfaces 56 on the top 20. This tilted position can be maintained by the attraction of a pair of magnets 40/42. It can be seen that tour tilted positions are possible with this arrangement, but two or more positions are obtainable when three or more balls/flats are employed.

A planar spring 62 is provided which is flexible in the direction of the rocking motion but it relatively rigid in its own plane. This relative rigidity prevents significant lateral relative movement between the top to and base 20/30.

The spring 62 is fixed to the base 30 by means of two posts 64 and is fixed to the top 20 by a further two posts 66. The cut-outs 68 in the spring allow the constrained rocking motion to take place, in this case, about a point located at the centre of ball 60. The spring 62 and other parts provide a quasi-kinematic support between the base and top.

Thus this arrangement provides three contact points between the top and base in any one of the table's tilted positions. The spring 62 prevents relative rotation of the top and base and lateral parallel movement between the two. A minimum of three contact points is required but more may be provided e.g. balls and vee grooves instead of balls and flats. No more than six contact points need be provided for each tilted position of the table.

In each of the embodiments shown in the Figures the tables may be tilted manually or may be tilted by being pushed by a movable part of the machine to which they are mounted, for example a contact probe may be used to push the table into the desired tilt position.

Alternatively some actuator may be used for example a solenoid 5 in FIG. 1 may be connected to a fixed part of the machine 4 and may move top element 20 between two tilt positions. Two actuators may be used if four tilt positions are required.

Other variants and modifications will be apparent to the skilled addressee, for example the location balls 34, 36, 52 and 54 may be supported on the base 30 and the vee blocks, slots, pads or triangular recess 32, 38, 50, 56 or 58 may be supported on the top 20. The balls need not all be supported on the top or base, neither need the vee blocks, slots, pads or recess all be supported on the top or base. Alternatives to the balls, vee blocks, slots, pads and, recess are, envisaged, e.g. in place of a vee block or slot 32, 38, 50 there may be provided a roller pair again giving two points of contact for a ball, or in place of a ball on a flat pad there nay be provided a pointed part. In place of a triangular recess there may be provided a nest of three balls. Thus, two, three or four or more tilt positions are possible. If three positions are required then a central 2-point contact e.g. a ball in a vee slot and three, outlying 2-point contacts may be provided.

Moreover the use of a kinematic support allows repeatable positioning by the arrangement of parts to provide generally six points of contact which constrain the six degrees of freedom of the top relative to the bottom. Such a kinematic support it sometimes known as a Boys support, and is described in, for example, H. J. J. Braddick, "Mechanical Design of Laboratory Apparatus", Chapman & Hall, London, 1960, pages 11–30.

Braddick also describes a functionally equivalent kinematic support, sometimes known as a Kelvin support, in which the six points of contact or constraints are provided three at a first location, two as a second spaced location, and one at a third spaced location. The terms "kinematic", "kinematically constrained" and like terms, as used in this specification, encompass Boys supports, Kelvin supports and other kinematic and semi- or quasi-kinematic types of supports. An example of a quasi-kinematic support is a cone and ball, a vee and ball and a flat and ball, the flat and vee providing two and one contact point between their respective balls and the cone providing nationally three (high spot) contact points at its ball.

It will be noted that the FIGS. 4 and 5 embodiment also has a quasi-kinematic arrangement, since the planar spring 62 constrains three degrees of freedom and the contact points constrain the other three.

The invention has been illustrated by its application to a workpiece-mounting table, for tilting the workpiece so that scanning of all its sides can take place. However, the invention may have any application where a tilting mechanism is useful. In the field of scanning this may be an application whereby a workpiece is held stationary and a part of the machine is moved using a tilting table according to the invention. Thus a laser may be tilted into any one of the positions of the tables mentioned above, if laser scanning is employed as a measurement technique. Alternatively part of the optical system e.g. a mirror may be tilted when using laser scanning. If touch scanning is used then the scanning stylus may be tilted using a table according to the invention. If camera type analysis of an object is required then the tilt table may be employed to tilt the object or the camera relative to the object, or to tilt part of the optics of the camera system relative to the object.

What is claimed is:

1. A tiltable table, comprising:

a first element;

a second element movable relative to the first element into two or more repeatable predetermined positions;

first support parts located at the first element; and second support parts located at the second element, wherein the first and second support parts are mutually co-operable to allow relative movement between the first and second elements into the two or more repeatable predetermined positions, to provide a kinematic support in each of the two or more positions, and to provide points of contact between the first and second support parts, and wherein the points of contact between the first and second support parts are different for each of the two or more repeatable predetermined positions.

2. The tiltable table as claimed in claim 1, wherein the first and second elements are held in each of the two or more repeatable predetermined positions by means of magnetic attraction.

3. The tiltable table as claimed in claim 1, wherein the tiltable table forms part of a machine and the machine has an actuator for causing the relative movement of the first and second elements.

4. The tiltable table as claimed in claim 3, wherein the actuator is selected from a group of actuators consisting of: a solenoid; a pneumatic movement device; a hydraulic movement device; and a movable part of the machine used as a pusher.

5. The tiltable table as claimed in claim 1, wherein one of the first and second support parts includes at least one ball and the relative movement between the first and second elements is a rotation about a central axis of the at least one ball.

6. A tiltable table, comprising:

a first element;

a second element movable relative to the first element into two or more repeatable predetermined positions;

first support parts located at the first element; and second support parts located at the second element, wherein the first and second support arts are mutually co-operable to allow relative movement between the first and second elements into the two or more repeatable predetermined positions, have no more than six points of contact when the first and second elements are in each of the two or more repeatable predetermined positions, restrict the relative movement of the first and second elements, and provide the points of contact between the first and second support parts, and wherein the points of contact between the first and second support parts are different for each of the two or more repeatable predetermined positions.

7. The tiltable table as claimed in claim 6, wherein the first and second elements are held in each of the two or more repeatable predetermined positions by means of magnetic attraction.

8. The tiltable table as claimed in claim 6, wherein the tiltable table forms part of a machine and the machine has an actuator for causing the relative movement of the first and second elements.

9. The tiltable table as claimed in claim 8, wherein the actuator is selected from a group of actuators consisting of: a solenoid; a pneumatic movement device; a hydraulic movement device; and a movable part of the machine used as a pusher.

10. The tiltable table as claimed in claim 6, wherein one of the first and second support parts includes at least one ball and the relative movement between the first and second elements is a rotation about a central axis of the at least one ball.

11. The tiltable table as claimed in claim 6, wherein the first and second support parts includes a resilient planar member providing resistance to the relative movement of the first and second element at least in a direction parallel to a plane of the resilient planar member.

* * * * *